United States Patent [19]

Koeffer et al.

[11] Patent Number: 4,947,005
[45] Date of Patent: Aug. 7, 1990

[54] PREPARATION OF 1,1,2-TRIALKOXYETHANES

[75] Inventors: Dieter Koeffer, Weinheim; Werner Bertleff, Viernheim, both of Fed. Rep. of Germany

[73] Assignee: BASF Aktiengesellschaft, Ludwigshafen, Fed. Rep. of Germany

[21] Appl. No.: 398,715

[22] Filed: Aug. 25, 1989

[30] Foreign Application Priority Data

Sep. 15, 1988 [DE] Fed. Rep. of Germany ....... 3831327

[51] Int. Cl.$^5$ .............................................. C07C 41/48
[52] U.S. Cl. .................................. 568/600; 568/591; 549/367; 549/374; 549/453
[58] Field of Search ................ 568/600, 591; 549/347, 549/374, 453

[56] References Cited

U.S. PATENT DOCUMENTS 2,449,470 7/1946 Gresham et al. .
4,755,625 4/1988 Maerkl et al. .

Primary Examiner—Howard T. Mars
Attorney, Agent, or Firm—John H. Shurtleff

[57] ABSTRACT 1,1,2-Trialkoxyethanes of the general formula I

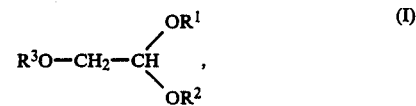
(I)

where $R^1$ to $R^3$ are each independently of the others $C_1$–$C_{20}$-alkyl or cycloalkyl, or $R^1$ and $R^2$ may be linked together to form a 5-, 6- or 7-membered ring, are prepared by reacting formaldehyde dialkyl acetals of the general formula II

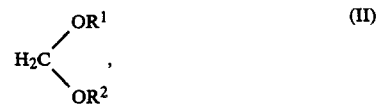
(II)

where $R^1$ and $R^2$ are each as defined above, or compounds which are capable of forming formaldehyde dialkyl acetals under the reaction conditions, with carbon monoxide, hydrogen and alkanols $R^3OH$ under superatmospheric pressure at elevated temperature in the presence of a catalyst composed of a cobalt carbonyl compound and a promotor, wherein the promotor is an alkali metal, alkaline earth metal or ammonium salt of a protogenic compound having an acid constant $K_a$ of from $10^{-2}$ to $10^{-14}$, an alkali metal or alkaline earth metal hydroxide or an aminocarboxylic acid.

4 Claims, No Drawings

PREPARATION OF 1,1,2-TRIALKOXYETHANES

The present invention relates to an improved process for preparing 1,1,2-trialkoxyethanes by reacting formaldehyde dialkyl acetals, or compounds which are capable of forming formaldehyde dialkyl acetals under the reaction conditions, with carbon monoxide, hydrogen and alkanols in the presence of a catalyst composed of a cobalt carbonyl compound and a promotor.

DE-A-No. 3,627,776 discloses that trialkoxyethanes can be prepared from formaldehyde acetals, carbon monoxide, hydrogen and alkanols by using a cobalt carbonyl catalyst which includes a phosphine, arsine, stibine or bismuthine promotor. The disadvantages of this process are, on the one hand, the relatively high cost of the promotors used and, on the other, their sensitivity to atmospheric oxygen.

US-A-No. 2,449,470 discloses that 1,1,2-trialkoxyethanes are obtained in the reaction of formaldehyde dialkyl acetals with carbon monoxide and hydrogen in the presence of an alkanol and a suspended cobalt oxide catalyst. The reaction pressure required is 600 bar or more.

DE-A-No. 890,945 discloses the preparation of 1,1,2-trimethoxyethane and ethylene glycol monomethyl ether from formaldehyde dimethyl acetal and a carbon monoxide/hydrogen gas mixture under superatmospheric pressure. The catalyst is said to be cobalt oxide on silica gel. The selectivity for trimethoxyethane leaves something to be desired.

It is an object of the present invention to provide a process for preparing 1,1,2-trialkoxyethanes which remedies the aforementioned disadvantages.

We have found that this object is achieved by an improved process for preparing a 1,1,2-trialkoxyethane of the general formula I

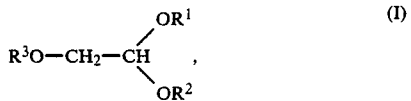

where $R^1$ to $R^3$ are each independently of the others $C_1$-$C_0$-alkyl or cycloalkyl, or $R^1$ and $R^2$ may be linked together to form a 5-, 6- or 7-membered ring, by reacting a formaldehyde dialkyl acetal of the general formula II

where $R^1$ and $R^2$ are each as defined above, or a compound which is capable of forming a formaldehyde dialkyl acetal under the reaction conditions, with carbon monoxide, hydrogen and an alkanol $R^3OH$ under superatmospheric pressure at elevated temperature in the presence of a catalyst composed of a cobalt carbonyl compound and a promotor, wherein the promotor is an alkali metal, alkaline earth metal or ammonium salt of a protogenic compound having an acid constant $K_a$ of from $10^{-2}$ to $10^{-14}$, an alkali metal or alkaline earth metal hydroxide or an aminocarboxylic acid.

The starting compound for the process according to the invention is a formaldehyde dialkyl acetal of the formula II

where $R^1$ and $R^2$ are each identical or different $C_1$-$C_{20}$-alkyl or cycloalkyl or are linked together to form a 5-, 6- or 7-membered ring. Preferably, $R^1$ and $R^2$ are each primary or secondary $C_1$-$C_8$-alkyl, in particular primary $C_1$-$C_4$-alkyl. Suitable cycloalkyl is $C_4$-$C_{12}$-cycloalkyl, preferably $C_4$-$C_8$-cycloalkyl, in particular $C_5$-$C_8$-cycloalkyl.

$R^1$ and $R^2$ are each for example methyl, ethyl, propyl, isopropyl, butyl, isobutyl, pentyl, hexyl, heptyl, octyl, 2-ethylhexyl, cyclopentyl, cyclohexyl or cyclooctyl. Cyclic acetals are, for example, 1,3-dioxolane and 1,3-dioxane. Instead of an acetal II it is also possible to use a precursor thereof, namely formaldehyde, or a compound which liberates formaldehyde under the reaction conditions, such as paraformaldehyde or trioxane, and the corresponding alcohol, in which case the ratio of aldehyde to alcohol can vary within wide limits. It is advantageous to use from 1 to 5 moles of alcohol per mole of aldehyde. Particular preference is given to reacting acetals where the alcohol component corresponds to the alcohol $R^3OH$ used for the reaction.

The alcohol $R^3OH$ is a $C_1$-$C_{20}$-alcohol, preferably a $C_1$-$C_8$-alcohol, in particular a $C_1$-$C_4$-alcohol. Possible alcohols are for example: methanol, ethanol, propanol, isopropanol, n-butanol, isobutanol, n-pentanol, isoamyl alcohol, neopentyl alcohol, n-hexanol, 2-hexanol, cyclohexanol, n-heptanol and n-octanol.

Formaldehyde dialkyl acetal II is reacted with an equimolar or higher amount of alcohol $R^3OH$ Advantageously, the alcohol can be used in excess, for example in an amount of from 1 to 5, preferably 1.1 to 4, in particular 1.5 to 2.5, moles of $R^3OH$ per mole of acetal. Higher excesses are possible, but do not produce any further benefits.

The hydroformylation of acetal II is accomplished with a carbon monoxide/hydrogen mixture in which from 0.5 to 1.5 moles, in particular from 0.5 to 1 moles, of hydrogen are present per mole of carbon monoxide. Preferably, the molar ratio of $CO:H_2$ is 1:1.

The process according to the invention is carried out in the presence of a catalyst composed of a cobalt carbonyl compound and a promotor, the promotor being an alkali metal, alkaline earth metal or ammonium salt of a protogenic compound having an acid constant $K_a$ of from $10^{-2}$ to $10^{-14}$, an alkali metal or alkaline earth metal hydroxide or an aminocarboxylic acid.

The cobalt carbonyl compound used can be for example dicobalt octacarbonyl or tetracarbonylhydridocobalt. The cobalt carbonyl compounds can also be prepared in situ from cobalt compounds which can form cobalt carbonyl complexes under the reaction conditions, such as cobalt salts of organic or inorganic acids, for example cobalt acetate, cobalt laurate, cobalt 2-ethylhexanoate, cobalt carbonate, cobalt nitrate or cobalt halides, or from cobalt oxide.

The promotor used can be an alkali metal, alkaline earth metal or ammonium salt, for example $Na_2HPO_4$, $Na_3PO_4$, $K_2HPO_4$, $K_3PO_4$, $KNH_4HPO_4$, lithium acetate, sodium acetate, potassium acetate, magnesium acetate, sodium propionate, sodium butyrate, sodium 2-ethylhexanoate, ammonium acetate or sodium phenoxide or an alkali metal or alkaline earth metal hydroxide, for example lithium hydroxide, sodium hydroxide, potassium hydroxide or calcium hydroxide, or an aminocarboxylic acid such as aminoacetic acid, 2-aminopropionic acid, 3-aminopropionic acid or 2-aminobutyric acid. Preferably, the promotor used is a compound which is soluble in the reaction mixture, for example the salt of a carboxylic acid, such as lithium acetate, sodium acetate, potassium acetate, magnesium acetate, potassium 2-ethylhexanoate, sodium stearate or potassium stearate. More particularly, the promotor used is a compound which in addition to having the abovementioned properties must be available at low cost, for example sodium acetate, sodium propionate, sodium 2-ethylhexanoate or aminoacetic acid.

The catalyst is advantageously prepared in situ from the cobalt carbonyl compound, or precursors thereof, and a promotor. The molar ratio of promotor to cobalt is in general from 0.1 to 2, preferably from 0.3 to 1.5.

The cobalt concentration can be set at from 0.01 to 6% by weight, based on the reaction mixture. Lower or higher concentrations are also possible.

The process according to the invention can be carried out in the presence or absence of a solvent. Suitable solvents are for example ethers such as diethyl or diphenyl ether, aromatic or aliphatic hydrocarbons such as benzene, toluene or hexane and alcohols. Advantageously, the alcohol $R^3OH$ required for the reaction also acts as the solvent.

The reaction can be carried out batchwise or preferably continuously at a pressure of from 100 to 700, in particular from 200 to 400 bar and at from 50 to 300° C., preferably from 100° to 250° C., by the customary techniques.

Afterwards the trialkoxyethane I can be isolated in a conventional manner, for example by distillation out of the mixture.

1,1,2-Trialkoxyethane is a versatile intermediate for organic syntheses. For example, by eliminating the acetal it is possible to prepare an alkoxyacetaldehyde, which can be condensed with formaldehyde to give polyols. By eliminating an alcohol it is also possible to prepare a dialkoxyethene, for example dimethoxyethene, which is the starting material for polymers.

EXAMPLES

EXAMPLES 1 TO 7

In an autoclave, 0.85 mol of methylal and 1.7 mol of methanol were hydroformylated at 150° C. and 280 bar in the course of 90 minutes in the presence of a catalyst composed of dicobalt octacarbonyl and a promotor, the ratio of carbon monoxide and hydrogen being 1:1. After cooling to room temperature and depressurizing the autoclave, the discharged reaction mixture was weighed and analyzed by gas chromatography. The runs are summarized in Table 1.

TABLE 1

| | Hydroformylation of methylal | | | | |
|---|---|---|---|---|---|
| Examples | Catalyst system | | Acid constant | Methylal conversion (%) | TMOE Selectivity[a] (%) |
| | $Co_2(CO)_8$ (mmol) | Promotor (mmol) | $K_a$ of corresponding acid[c] | | |
| 1 | 3 | — | — | 70 | 35 |
| 2 | 3 | 1.2 $NaH_2PO_4$ | $H_3PO_4$ $10^{-2.16}$ | 68 | 45 |
| 3 | 3 | 1.2 $Na_2HPO_4$ | $H_2PO$ $10^{-7.21}$ | 60 | 50 |
| 4 | 3 | 3 $NaCH_3COO$ | $CH_3COOH$ $10^{-4.75}$ | 61 | 51 |
| 5 | 3 | 6 $NaCH_3COO$ | $CH_3COOH$ $10^{-4.75}$ | 50 | 59 |
| 6 | 3 | 15 $NaCH_3COO$ | $CH_3COOH$ $10^{-4.75}$ | — | — |
| 7[b] | 1.5 | 1.5 $NH_2CH_2COOH$ | | 63 | 54 |

[a]TMOE: 1,1,2-trimethoxyethane
[b]250 bar, $CO/H_2$ 1:1, 150° C., 1.5 h; 0.42 mol of methylal, 0.84 mol of methanol
[c]Ref.: Holleman-Wiberg, Lehrbuch der Anorganischen Chemie, 91st-100th edition, pages 196-199, 241, Walter de Gruyter, Berlin, New York, 1985.

EXAMPLE 8 TO 16

The method of Examples 1 to 7 was repeated to react 0.4 mol of butylal and 0.8 mol of butanol in the presence of 4 mmol of dicobalt octacarbonyl and various promoters. The runs are summarized in Table 2.

TABLE 2

| | Hydroformylation of butylal | | | | | |
|---|---|---|---|---|---|---|
| Examples | Promotor (mole/mole of CO) | | Acid constant $K_a$ of corresponding acid[d] | Butylal conversion (%) | Selectivity (%) | | |
| | | | | | TBOE | BEG | BOA |
| 8 | — | | — | 97 | 24 | 19 | 3 |
| 9 | 0.6 | $KCH_3COO$ | $CH_3COOH$ $10^{-4.75}$ | 53 | 58 | 9 | 10 |
| 10 | 0.3 | NaOH | $H_2O$ $10^{-14}$ | 83 | 52 | 13 | 7 |
| 11 | 0.6 | NaOH | $H_2O$ $10^{-14}$ | 70 | 50 | 16 | 9 |
| 12 | 0.3 | $Na_3PO_4$ | $HPO_4^{2-}$ $10^{-12.3}$ | 76 | 43 | 15 | 8 |
| 13 | 0.3 | $Na_2HPO_4$ | $H_2PO_4^-$ $10^{-7.21}$ | 91 | 33 | 20 | 6 |
| 14 | 0.6 | $NaH_2PO_4$ | $H_3PO_4$ $10^{-2.16}$ | 94 | 30 | 21 | 6 |
| 15 | 0.6 | NaCl | HCl $10^{+7.0}$ | 98 | 17 | 16 | 2 |

TABLE 2-continued

| | | Hydroformylation of butylal | | | | |
|---|---|---|---|---|---|---|
| Examples | Promotor (mole/mole of CO) | Acid constant $K_a$ of corresponding acid[d] | Butylal conversion (%) | Selectivity (%) | | |
| | | | | TBOE | BEG | BOA |
| 16 | 0.6 $Na_2SO_4$ | $HSO_4^-$  $10^{-1.96}$ | 94 | 26 | 11 | 5 |

Abbreviations:
BOA: butoxyacetaldehyde
TBOE: 1,1,2-tributoxyethane
BEG: ethylene glycol monobutyl ether
[d]cf. footnote c to Table 1.

EXAMPLE 17

In a 360 ml capacity tubular reactor with a continuous upward flow, 9800 g of a reaction solution, containing 4870 g (64.1 mol) of methylal, 4360 g (136.3 mol) of methanol, 457.5 g (1.33 mol) of cobalt 2-ethylhexanoate and 65.1 g (0.79 mol) of sodium acetate, were hydroformulated at 250 bar and 150° C. in the course of an average reaction time of 30 minutes. The solution initially contained 0.5% of water from the starting materials. The ratio of carbon monoxide to hydrogen was 1:1. After depressurization and cooling, the discharged reaction mixture, amounting to 10,454 g, had the following composition by gas chromatography: 3753 g (49.4 mol) of methylal, 3910 g (122.2 mmol) of methanol, 1516 g (12.6 mol) of 1,1,2-trimethoxyethane, 314 g (17.4 mol) of water, 31.9 g (0.4 mol) of ethylene glycol monomethyl ether and 63 g (0.9 mol) of methoxyacetaldehyde, plus unspecified high boilers and catalyst.

We claim:

1. In a process for preparing a 1,1,2-trialkoxyethane of the formula

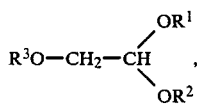

where $R^1$ to $R^3$ are each independently of the others $C_1$-$C_{20}$-alkyl or cycloalkyl, or $R^1$ and $R^2$ may be linked together to form a 5-, 6- or 7-membered ring, by reacting a formaldehyde dialkyl acetal of the formula

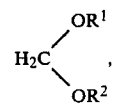

where $R^1$ and $R^2$ are each as defined above, or a compound which is capable of forming a formaldehyde dialkyl acetal under the reaction conditions, with carbon monoxide, hydrogen and an alkanol $R^3OH$ under superatmospheric pressure at elevated temperature in the presence of a catalyst composed of a cobalt carbonyl compound and a promotor, the improvement which comprises using as the promotor an alkali metal, alkaline earth metal or ammonium salt of a protogenic compound having an acid constant $K_a$ of from $10^{-2}$ to $10^{-14}$, an alkali metal or alkaline earth metal hydroxide or an aminocarboxylic acid.

2. A process as claimed in claim 1, wherein the promotor is an alkali metal, alkaline earth metal or ammonium salt of a carboxylic acid.

3. A process as claimed in claim 1, wherein from 0.1 to 2 moles of promotor are used per mole of cobalt.

4. A process as claimed in claim 1, wherein formaldehyde, or a compound which liberates formaldehyde under the reaction conditions, is used with the alkanol reactant $R^3OH$ to form the acetol reactant.

* * * * *